United States Patent
Takahashi et al.

(10) Patent No.: US 6,841,653 B2
(45) Date of Patent: Jan. 11, 2005

(54) THIOL CARBOXYLATE ESTER AND ITS STABILIZATION PROCESS

(75) Inventors: Yoshiyuki Takahashi, Kyoto (JP); Yoichi Hino, Takaishi (JP); Tatsuhito Matsuda, Kobe (JP)

(73) Assignee: Nippon Shokubai Co., Ltd., Osaka (JP)

(*) Notice: Subject to any disclaimer, the term of this patent is extended or adjusted under 35 U.S.C. 154(b) by 0 days.

(21) Appl. No.: 10/385,725

(22) Filed: Mar. 9, 2003

(65) Prior Publication Data

US 2003/0187288 A1 Oct. 2, 2003

(30) Foreign Application Priority Data

Mar. 25, 2002 (JP) .................................. 2002-083999
Apr. 26, 2002 (JP) .................................. 2002-127567

(51) Int. Cl.$^7$ .................... C08G 75/04; C07C 327/00
(52) U.S. Cl. .................... 528/375; 528/373; 558/251; 558/250
(58) Field of Search ................ 558/251, 250; 528/375, 373

(56) References Cited

U.S. PATENT DOCUMENTS

| 4,751,263 | A | 6/1988 | Domeier et al. |
| 6,342,571 | B1 | 1/2002 | Smith et al. |
| 6,518,393 | B2 * | 2/2003 | Primel et al. ............... 528/375 |

FOREIGN PATENT DOCUMENTS

| EP | 0 273 661 A1 | 7/1988 |
| EP | 0 273 710 A2 | 7/1988 |

OTHER PUBLICATIONS

Matsuda et al., Novel Bifunctional Thiolcarboxylic Acid Esters Useful As Crosslinking Agents For Optical Materials, Synthetic Communications, 2000, 3041–3045, 30 (16), Nippon Shokubai Co. Ltd, Ibaraki, Japan.

Matsuda et al., High Index Optical Materials Prepared By Copolymerization Of Novel Bifunctional Thiomethacrylates, I.M.S.–Pure Appl. Chem., 2000, 239–257, A37(3), Nippon Shokubai Co. Ltd., Ibaraki, Japan.

* cited by examiner

*Primary Examiner*—Rita Desai
*Assistant Examiner*—Robert Shiao

(57) ABSTRACT

A thiol carboxylate ester as shown by general formula (I) below, which has a half ester content of 0.0001 to 2 mass %, and favorably, which has a halogen content of not more than 2 mass % and/or to which a polymerization inhibitor such as a catechol family member is added.

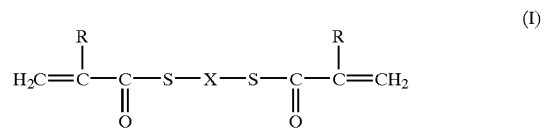

4 Claims, No Drawings

THIOL CARBOXYLATE ESTER AND ITS STABILIZATION PROCESS

BACKGROUND OF THE INVENTION

A. Technical Field

The present invention relates to: a thiol carboxylate ester which is excellent in polymerizability and in stability even if stored for a long term; and a process for stabilizing a thiol carboxylate ester.

B. Background Art

As to high refractive materials, inorganic optical materials such as glass are recently becoming replaced with high transparent synthetic resins. So they are, particularly, in the use for such as contact lenses. The high refractive resins are good in their light weight property, impact resistance, molding-processibility, and dyeability, therefore their field of application as optical plastic materials is extending.

However, dialkylene glycol bis(ally carbonate) resins, which are widely used as the optical plastic materials, have an insufficient refractive index of 1.49 to 1.50. Therefore, optical lenses obtained from these resins have a demerit in that the thicknesses of their centers and edges are larger than those of inorganic optical lenses.

In order to solve such problems, the present applicant developed a novel thiol carboxylate ester as shown by general formula (I) below (JP-A-162671/1988):

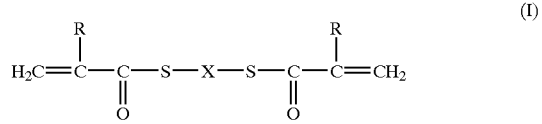

(wherein: R denotes H or —$CH_3$; and X denotes —$CH_2CH_2SCH_2CH_2$—, —$CH_2CH_2OCH_2CH_2$—, or —$CH_2CH_2$—).

This substance is a monomer which gives a resin having so high a refractive index and so excellent transparency as to be useful as an optical plastic material.

However, thereafter, it has turned out that: this monomer may have problems in point of its polymerizability, and further, when this monomer is stored for a long term, its stability, particularly, coloring, may be problematic, specifically, depending on conditions for polymerization or use of this monomer, its slightly low polymerizability or its stability during its long-term storage may be problematic. If the polymerizability of the monomer is slightly low, there is a concern about that there may occur problems in point of such as processibility (e.g. cutting property) and mechanical properties of a molded structure obtained by polymerization of the monomer. In addition, in the case where the monomer has colored as a result of the long-term storage, there is a concern about that, when this monomer is polymerized and then used as an optical plastic material, its transparency and refractive index may be low.

JP-A-199963/1994 discloses a process for polymerizing a thiol carboxylate ester containing a Michael addition product, but is silent about that the thiol carboxylate ester used as a monomer may have problems in point of its polymerizability and stability.

Incidentally, unless otherwise noted, the polymerizability, as herein referred to, means the polymerizability of the monomer in its polymerization reaction which is carried out in such as the resin-forming step (polymerization step). In addition, the stability as herein referred to is a performance concerning the quality of the monomer such as coloring inhibitability and storage stability.

SUMMARY OF THE INVENTION

A. Object of the Invention

Thus, an object of the present invention to solve the above problems is to provide a thiol carboxylate ester and its stabilization process, which thiol carboxylate ester is excellent in polymerizability and good in stability, particularly colors little, even if stored for a long term, and which thiol carboxylate ester is therefore a monomer useful as an optical plastic material or as a transparent plastic material.

B. Disclosure of the Invention

The present inventors diligently studied to solve the above problems. In the process of this study, they inferred that, as to the coloring which might occur during the long-term storage, a cause thereof might be the slight polymerization of the thiol carboxylate ester during the long-term storage, and thus they attempted to add various polymerization inhibitors, but could not obtain any very good results. On the other hand, as to the problems in point of the slightly low polymerizability, the present inventors conceived that causes of those problems might be very small amounts of substances as contained in the thiol carboxylate ester, and thus they attempted also to repeat the distillation purification of the thiol carboxylate ester as obtained by the synthesis process, but the problems of the slightly low polymerizability could not be solved by the distillation purification, either.

The present inventors, thus, tried probing into what the very small amounts of substances as contained in the thiol carboxylate ester are and how those substances become contained. As a result, they have completed the present invention by finding out that: in the synthesized thiol carboxylate ester, there are contained an ester as shown by general formula (II) below (hereinafter this ester is referred to as half ester) and a halogen, and the problem of the slightly low polymerizability and the problem of the stability (e.g. prevention of the coloring during the long-term storage) can both surely be solved by defining, of their contents, at least the half ester content in a specific range;

wherein the general formula (II) is:

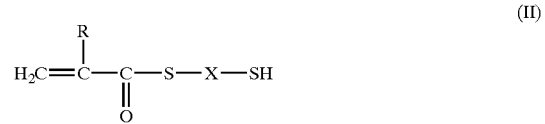

(wherein: R denotes H or —$CH_3$; and X denotes —$CH_2CH_2SCH_2CH_2$—, —$CH_2CH_2OCH_2CH_2$—, or —$CH_2CH_2$—).

According to the present inventors' view, the above half ester contains an SH group at an end of its molecule and therefore has an effect on the prevention of the polymerization reaction of the thiol carboxylate ester. Accordingly, if the half ester is present in a large amount in the thiol carboxylate ester, the polymerizability of the thiol carboxylate ester is retarded, so there is a concern about that there may occur problems in point of such as deterioration of processibility (e.g. cutting property) and mechanical properties of the molded structure as obtained by polymerization using the thiol carboxylate ester as a monomer. According to the present inventors' findings, the upper limit of the half ester content for the half ester not to cause the polymerization retardation is 2 mass % relative to the thiol carboxylate ester. On the other hand, that the half ester has the polymerization retardation action on the thiol carboxylate ester means, in other words, that, if the half ester is present in a very small amount in a specific range in the thiol carboxylate ester, there is also an effect of preventing the stability inhibition (e.g. coloring) caused by the slight polymerization of the thiol carboxylate ester with the passage of time. According to the present inventors' findings, if the half ester is present in the thiol carboxylate ester in a ratio of not less than 0.0001 mass % relative to the thiol carboxylate ester, the stability of the thiol carboxylate ester is enhanced. In short, the problem of the slightly low polymerizability and the problem of the stability (e.g. prevention of the coloring during the long-term storage) can both be solved by defining the half ester content in the range of 0.0001 to 2 mass % relative to the thiol carboxylate ester.

Accordingly, a thiol carboxylate ester according to the present invention is a thiol carboxylate ester as shown by the above general formula (I), and is characterized by having a half ester content of 0.0001 to 2 mass % relative to the thiol carboxylate ester.

In addition, a process for stabilizing a thiol carboxylate ester, according to the present invention, is a process comprising the step of, when producing the thiol carboxylate ester as shown by the above general formula (I), adjusting the half ester content of the thiol carboxylate ester to 0.0001 to 2 mass % relative to the thiol carboxylate ester.

For still more enhancing the stability of the thiol carboxylate ester (for example, by preventing its coloring during its long-term storage), it is favorable to adjust the halogen content of the thiol carboxylate ester to not more than 2 mass % relative to the thiol carboxylate ester and/or add a polymerization inhibitor to the thiol carboxylate ester in a ratio of 0.001 to 2 mass % relative to the thiol carboxylate ester. As the polymerization inhibitor, there is favorably used a catechol family member.

These and other objects and the advantages of the present invention will be more fully apparent from the following detailed disclosure.

DETAILED DESCRIPTION OF THE INVENTION

Examples of the thiol carboxylate ester as shown by the general formula (I) include bis(2-(meth)acryloylthioethyl) sulfide of chemical formula (1) below, bis(2-(meth) acryloylthioethyl) ether of chemical formula (2) below, and 1,2-bis(2-(meth)acryloylthio)ethane of chemical formula (3) below (wherein the "(meth)acryloyl" means: "acryloyl" when R is H in the following chemical formulae (1) to (3); and "methacryloyl" when R is —CH$_3$ in them).

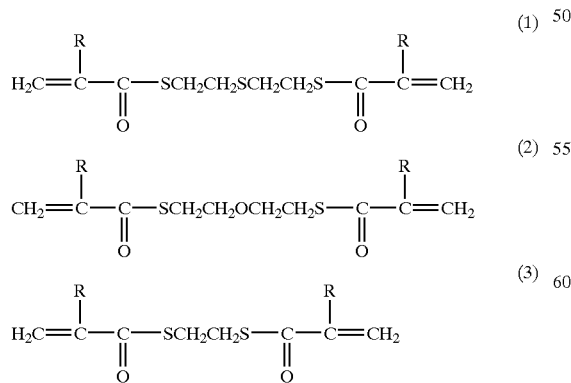

The thiol carboxylate ester as shown by the general formula (I) can be produced by a process including the step of carrying out a reaction, as shown by formula (III) below, between a dithiol derivative thiol family member and a (meth)acrylic acid derivative (refer to such as JP-A-162671/1988 and JP-A-003675/1990) and also can be produced by a process including the step of carrying out a reaction between (meth)acrylic anhydride and a polythiol (refer to JP-A-199963/1994), wherein the formula (III) is:

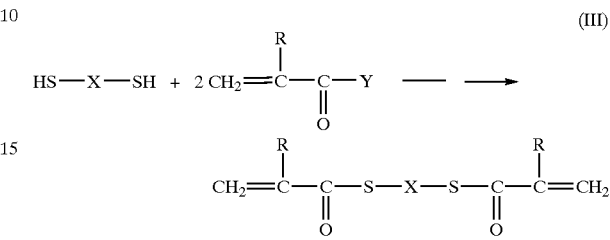

(wherein: R denotes H or —CH$_3$; X denotes —CH$_2$CH$_2$SCH$_2$CH$_2$—, —CH$_2$CH$_2$OCH$_2$CH$_2$—, or —CH$_2$CH$_2$—; and Y denotes Cl, Br, OH, or any of C$_1$ to C$_4$ alkoxy groups).

When the thiol carboxylate ester is produced by such as the above process, a half ester (b) is formed as a by-product in a way as shown by the following reaction formula (IV):

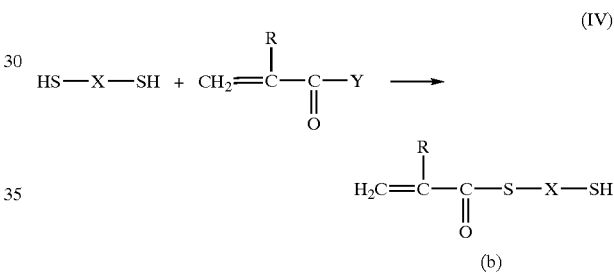

(wherein: R denotes H or —CH$_3$; X denotes —CH$_2$CH$_2$SCH$_2$CH$_2$—, —CH$_2$CH$_2$OCH$_2$CH$_2$—, or —CH$_2$CH$_2$—; and Y denotes Cl, Br, OH, or any of C$_1$ to C$_4$ alkoxy groups).

For example, in the case where a reaction between bis(2-mercaptoethyl) sulfide and the (meth)acryloyl chloride derivative is carried out, a half ester of the following chemical formula (b1), namely, (2-(meth)acryloylthioethyl) 2'-mercaptoethyl sulfide, is formed as a by-product.

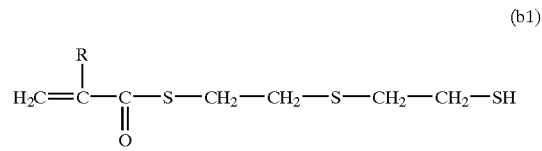

The above half ester is difficult to remove by conventional distillation purification. The half ester content can be controlled by adjusting the production conditions when producing the thiol carboxylate ester and, for example, can be optimized by adjusting such as: the amounts of the (meth) acryloyl chloride derivative and the thiol family member as mixed together; their dropwise addition initiation temperatures and dropwise addition durations; and the aging duration after their dropwise additions; as follows.

The ratio between the (meth)acryloyl chloride derivative and the thiol family member as mixed together is favorably in the range of ((meth)acryloyl chloride derivative):(thiol family member)=(0.5:1) to (6:1), more favorably in the range of ((meth)acryloyl chloride derivative):(thiol family member)=(1.25:1) to (4:1), in terms of molar ratio.

The dropwise addition initiation temperatures are favorably in the range of 2 to 15° C., more favorably 5 to 10° C.

The dropwise addition durations are favorably in the range of 0.3 to 3 hours, more favorably 0.5 to 1.5 hours.

Particularly the aging duration, after the dropwise additions, has a great influence on the stability, and is favorably in the range of 0.5 to 3 hours, more favorably 0.5 to 2 hours.

By controlling the production conditions in the above way, the half ester content is adjusted into the range of 0.0001 to 2 mass % relative to the thiol carboxylate ester. Hereupon, the half ester content is mass % of the half ester relative to the thiol carboxylate ester. In the case where this half ester content is less than 0.0001 mass %, the stability of the thiol carboxylate ester tends to be low. In the case where the half ester content is more than 2 mass %, the polymerization of the monomer tends to result in being insufficient in the subsequent resin-forming step (polymerization step). The lower limit of the half ester content is favorably 0.001 mass %, more favorably 0.01 mass %. The upper limit of the half ester content is favorably 1 mass %, more favorably 0.8 mass %.

Incidentally, the half ester content can be quantitatively analyzed by conventional gas chromatography.

There is a case where the thiol carboxylate ester as obtained by the synthesis process contains an organohalogen compound (e.g. Cl⁻, Br⁻, chloroform, methylene chloride, carbon tetrachloride, chloroethane, dibromomethane, chlorobenzene) as other impurities besides the half ester. As to the coloring which may occur during the long-term storage, the organohalogen compound also has a great influence thereon. Therefore, its content needs to be suppressed to not more than 2 mass % relative to the thiol carboxylate ester. In the case where the halogen content is more than 2 mass % relative to the thiol carboxylate ester, the degree of coloring during the long-term storage tends to increase. The upper limit of the halogen content relative to the thiol carboxylate ester is favorably 1.0 mass %, more favorably 0.5 mass %, most favorably 0.1 mass %. Incidentally, the halogen content may be 0 mass %. However, in the industrial production, a high cost or a lot of steps are needed for rendering the halogen content 0 mass %, and its achievement is difficult. Therefore, the lower limit of the halogen content relative to the thiol carboxylate ester is favorably 0.0001 mass %, more favorably 0.001 mass %, most favorably 0.005 mass %.

In the present invention, the aforementioned half ester content and the abovementioned halogen content, relative to the thiol carboxylate ester, favorably satisfy both the above ranges at the same time.

The halogen content as herein referred to is defined as mass % of halogen atoms, existing in the halogen compound, relative to the thiol carboxylate ester as follows:

Halogen content (mass %)=[(halogen compound content (mass %) relative to thiol carboxylate ester)×(atomic weight of halogen)×(mols of halogen per 1 mol of halogen compound)]÷(molecular weight of halogen compound)

The halogen compound content can be quantitatively analyzed by conventional gas chromatography.

The halogen compound content can be decreased by causing a gas to accompany the solvent when distilling it off after the reaction, and it is also one method therefor to cause the gas (e.g. air, nitrogen, inert gas) to flow in from the bottom. As to the gas, air is favorably used in view of its easy availability. The halogen compound content can be optimized by adjusting such as: the bottom temperature and the amount of the gas during the distillation; and the distillation duration; for example, as follows.

The bottom temperature during the distillation is favorably lower than 60° C., more favorably lower than 40° C.

The flow rate of the gas is favorably in the range of 0.01 to 10 liters/h, more favorably 0.1 to 2.0 liters/h, per bottom amount (1 kg).

Particularly the distillation duration has a great influence on the halogen compound content, and is favorably in the range of 1.0 to 100 hours, more favorably 2.5 to 50 hours.

In the present invention, if a defined amount of a polymerization inhibitor is added to the thiol carboxylate ester containing the half ester in the defined amount range and, according to circumstances, further containing the halogen in not larger than the defined amount, then the stability of the thiol carboxylate ester is still more enhanced. In the present invention, how to add the polymerization inhibitor is not limited. The polymerization inhibitor may be added either before the production of the thiol carboxylate ester, or during or after this production. A portion of the polymerization inhibitor may be added before or during the above production, and thereafter the rest may further additionally be added.

The amount of the polymerization inhibitor which may be added to the thiol carboxylate ester is in the range of 0.001 to 2 mass % relative to the thiol carboxylate ester. Hereupon, the amount of the polymerization inhibitor as added is mass % of the polymerization inhibitor relative to the thiol carboxylate ester. In the case where this amount as added is smaller than 0.001 mass %, the degree of coloring tends to increase. In the case where the above amount as added is larger than 2 mass %, it tends to be difficult to polymerize the thiol carboxylate ester. The lower limit of the amount of the polymerization inhibitor as added is favorably 0.01 mass %, more favorably 0.1 mass %. The upper limit of the amount of the polymerization inhibitor as added is favorably 1 mass %, more favorably 0.5 mass %.

Examples of the polymerization inhibitor include hydroquinone, phenothiazine, p-methoxyphenol, benzoquinone, and hindered amines, and besides, a catechol family member. However, the use of the catechol family member is the most favorable for obtaining more stability (particularly, preventing the coloring during the long-term storage).

Incidentally, the catechol family member, which is herein referred to, is an aromatic compound which possesses at least two hydroxyl groups and in which at least one pair of hydroxyl groups are substituted at adjacent positions, and this catechol family member is favorably shown by general formula (4) below. Specific examples thereof include catechol, methylcatechol, t-butylcatechol, and di-t-butylcatechol.

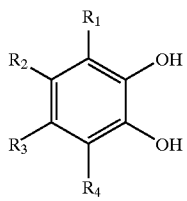

(4)

(wherein each of $R_1$, $R_2$, $R_3$, and $R_4$ denotes a hydrogen atom, a hydroxyl group, or any of alkyl groups having 1 to 4 carbon atoms)

The thiol carboxylate ester, according to the present invention, of the general formula (I) is not limited only to that which contains the half ester in the defined amount and, according to circumstances, further contains the halogen in not larger than the defined amount and, if necessary, to which the polymerization inhibitor is added in the ratio of 0.001 to 2 mass %, but the thiol carboxylate ester, according to the present invention, may be a composition in which there coexist the above components and another compound (A).

Examples of the above other compound (A) include: solvents; compounds formed as by-products during the synthesis; and additives other than the polymerization inhibitors; but favorably, those which do not influence the stability of the thiol carboxylate ester which is one of the effects of the present invention. In addition, the compound (A) may be the Michael addition product as contained in the thiol carboxylate ester as disclosed in JP-A-199963/1994. The amount of the above other compound (A) as added will do if it does not exceed the amount of the thiol carboxylate ester. For example, it is not larger than 50 mass %, favorably not larger than 30 mass %, more favorably not larger than 20 mass %, most favorably not larger than 10 mass %, relative to the thiol carboxylate ester.

Such a composition containing the thiol carboxylate ester may be either a reaction liquid itself of the thiol carboxylate ester as obtained by the aforementioned synthetic process, or a composition in which the purity of the thiol carboxylate ester has been enhanced by purification.

The thiol carboxylate ester, according to the present invention, displays a degree of coloring (Hazen) of not more than 120 as a result of storage in an incubator of 40° C. for 30 days. In a favorable mode for carrying out the present invention, the degree of coloring (Hazen) is not more than 100, more favorably not more than 80, still more favorably not more than 60, yet still more favorably not more than 50. However, in the best mode for carrying out the present invention, the degree of coloring (Hazen) is not more than 40.

The thiol carboxylate ester, according to the present invention, can be homopolymerized, or copolymerized with various compounds having an olefinic double bond, to thereby obtain a polymer or oligomer having excellent transparency. The resultant resin has a high refractive index, and further is good in processibility for such as cutting and polishing because of being a three-dimensionally crosslinked product. Therefore this resin is suitable as an optical plastic.

(Effects and Advantages of the Invention):

The thiol carboxylate ester, according to the present invention, is good in polymerizability and still more stable in quality even for a long storage term, and is therefore, for example, able to give extremely high transparency to resins as obtained from this thiol carboxylate ester.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited thereto.

Hereinafter, the unit "part(s)" is "mass part(s)".

A thiol carboxylate ester of the general formula (I) was produced in the following way, and its stability was examined on the basis of the degree of coloring as a result of a heat-resistant discoloring test comprising the steps of: placing the resultant thiol carboxylate ester into a wide-mouthed glass bottle of 200 ml in capacity in such a manner that the upper gas space of this bottle would be 20 volume % of its entire capacity; and then displacing the internal air of this bottle with nitrogen; and then retaining this bottle at 40° C. in an airtight state for 30 days. The evaluation of the degree of coloring (Hazen) was judged and measured by eye measurement comparison with a standard liquid on the basis of Hazen's color number method according to JIS K6901 5.2.1. The polymerizability was evaluated by examining the cutting processibility of a molded structure as obtained by using the thiol carboxylate ester as a monomer.

Incidentally, the amounts of the thiol carboxylate ester, the half ester, and the organohalogen compound, as contained in the resultant compositions, were quantitatively analyzed by the following method.

Analytical method: the thiol carboxylate ester content, the organohalogen compound content, and the half ester content were quantitatively analyzed by the internal standard method with a gas chromatograph (GC14A, produced by Shimadzu Corporation) using a capillary column (TC17, produced by GL Science).

EXAMPLE 1-1

An amount of 0.31 part of tetra-n-butylammonium hydrogensulfate, 0.13 part of p-methoxyphenol, and 668 parts of chloroform were-charged into an airtight container as equipped with a stirrer, a thermometer, a condenser, and droppers. While the inside temperature was kept at not higher than 15° C., there began to be dropwise added a mixed liquid (as separately prepared from 71.0 parts of bis(2-mercaptoethyl) sulfide and 953 parts of a 6.5 mass % aqueous potassium hydroxide solution) and 101.0 parts of methacryloyl chloride from their respective droppers in the inside temperature range of 6 to 10° C. Then, while the inside temperature was kept at not higher than 15° C., these dropwise additions had been completed in 1 hour. Thereafter, the stirring was further continued at lower than 20° C. for 1 hour, and then the resultant reaction solution was separated into two layers, namely, a chloroform layer and a water layer. After the water layer had been removed, the residual chloroform solution was washed with a 5 mass % aqueous potassium hydroxide solution and water in order.

Next, while a container, in which the washed chloroform solution was placed, was heated from the bottom of the container with caution for the bottom temperature of the chloroform solution not to exceed 40° C., air was caused to flow in from the bottom of the container under a pressure of 2.67×10⁴ Pa to cause the chloroform solution to bubble, thereby distilling off the chloroform in 40 hours to obtain 123 parts of a dehalogenated solution consisting of a composition containing bis(2-methacryloylthioethyl) sulfide (which is a thiol carboxylate ester), (2-methacryloylthioethyl) 2'-mercaptoethyl sulfide (which is a half ester), and chloroform (which is an organohalogen compound). Incidentally, the above (2-methacryloylthioethyl) 2'-mercaptoethyl sulfide is a compound such that: in the general formula (II), R is a methyl group; and X is —$CH_2CH_2SCH_2CH_2$—.

As a result of the quantitative analysis of the above dehalogenated solution, the thiol carboxylate ester (bis(2-methacryloylthioethyl) sulfide) content was 93.0 mass % (relative to the dehalogenated solution), and the half ester ((2-methacryloylthioethyl) 2'-mercaptoethyl sulfide) content was 0.3 mass % (relative to the thiol carboxylate ester), and the organohalogen compound (chloroform) content was 0.01 mass % (relative to the thiol carboxylate ester).

An amount of 0.11 part of methylcatechol (0.22 mass % relative to the thiol carboxylate ester) was added to and uniformly dissolved into 53.8 parts (50 parts as pure thiol carboxylate ester component) of the dehalogenated solution (degree of coloring: Hazen 20) (as obtained above), and the resultant methylcatechol-added dehalogenated solution was placed into a wide-mouthed bottle, and then the internal air of this bottle was displaced with nitrogen, and then this bottle was made airtight and then stored in an incubator of 40° C. for 30 days. After the passage of 30 days, the degree of coloring, as evaluated, was Hazen 30.

An amount of 100 parts of the above-obtained dehalogenated solution (having the bis(2-methacryloylthioethyl) sulfide content of 93.0 mass % and the half ester content of 0.3 mass % relative to this thiol carboxylate ester) was mixed with 0.5 part of 2,2'-azobis(2,4-dimethylvaleronitrile), and the resultant mixture was cast-polymerized with a mold (comprising two glass plates and a gasket made of silicone rubber) at the temperatures as elevated stepwise in sequence of 50° C. for 6 hours, 60° C. for 16 hours, and 90° C. for 2 hours, thus obtaining a 3-mm-thick sheet made of the thiol carboxylate ester. This sheet was cut with a diamond cutter to observe whether the cut section was broken, cracked, fused, or not. As a result, in the cut section, there was seen none of breakage, cracks, and fusion. Therefrom the above-obtained thiol carboxylate ester was found to be good in polymerizability.

EXAMPLES 1-2 TO 1-7 AND COMPARATIVE EXAMPLES 1-1 TO 1-2

Dehalogenated solutions containing the thiol carboxylate ester were obtained in the same way as of Example 1-1 except that the stirring duration, after the completion of the dropwise additions, and the distillation duration of the chloroform, were changed.

With regard to the resultant dehalogenated solutions, the quantitative analyses of their thiol carboxylate ester contents, half ester contents, and organohalogen compound contents and further their heat-resistant discoloring tests were carried out in the same way as of Example 1-1. Their results are shown in Table 1.

EXAMPLE 1-8

A thiol carboxylate ester was obtained in the same way as of Example 1-1 except that p-methoxyphenol was added in place of the methylcatechol. Its heat-resistant discoloring test showed a degree of coloring of Hazen 60. The results are shown in Table 1.

EXAMPLE 1-9

A dehalogenated solution containing the thiol carboxylate ester was obtained in the same way as of Example 1-1 except that the methylcatechol was not added. Its heat-resistant discoloring test showed a degree of coloring of Hazen 90. The results are shown in Table 1.

EXAMPLE 1-10

A dehalogenated solution containing the thiol carboxylate ester was obtained in the same way as of Example 1-1 except that the distillation duration of the chloroform was shortened to 0.5 hour.

With regard to the resultant dehalogenated solution, the quantitative analysis of its organohalogen compound content and further its heat-resistant discoloring test were carried out in the same way as of Example 1-1. Their results are shown in Table 1.

EXAMPLE 1-11

A dehalogenated solution containing the thiol carboxylate ester was obtained in the same way as of Example 1-1 except that the distillation duration of the chloroform was shortened to 0.5 hour and that the addition of the polymerization inhibitor was omitted.

With regard to the resultant dehalogenated solution, the quantitative analysis of its organohalogen compound content and further its heat-resistant discoloring test were carried out in the same way as of Example 1-1. Their results are shown in Table 1.

EXAMPLE 1-12

An amount of 0.65 part of tetra-n-butylammonium hydrogensulfate, 0.24 part of methylcatechol, and 1,000 parts of chloroform were charged into an airtight container as equipped with a stirrer, a thermometer, a condenser, and droppers. There began to be dropwise added a mixed liquid (as separately prepared from 79.8 parts of bis(2-mercaptoethyl) sulfide and 1,071 parts of a 6.5 mass % aqueous potassium hydroxide solution) and 179.0 parts of methacryloyl chloride from their respective droppers in the inside temperature range of 6 to 10° C. Then, while the inside temperature was kept at not higher than 15° C., these dropwise additions had been completed in 1 hour. Thereafter, the stirring was further continued at lower than 20° C. for 1 hour, and then the resultant reaction solution was separated into two layers, namely, a chloroform layer and a water layer. After the water layer had been removed, the residual chloroform solution was washed with a 4 mass % aqueous potassium hydroxide solution and water in order.

Next, while a container, in which the washed chloroform solution was placed, was heated from the bottom of the container with caution for the bottom temperature of the chloroform solution not to exceed 40° C., air was caused to flow in from the bottom of the container under a pressure of $2.67 \times 10^4$ Pa to cause the chloroform solution to bubble, thereby distilling off the chloroform in 40 hours to obtain a dehalogenated solution containing the thiol carboxylate ester.

With regard to the resultant dehalogenated solution, the quantitative analysis of its organohalogen compound content and further its heat-resistant discoloring test were carried out in the same way as of Example 1-1. Their results are shown in Table 1.

TABLE 1

| Example and Comparative Example | Stirring duration after completion of dropwise additions (h) | Distillation duration of solvent (h) | Thiol carboxylate ester (mass %) | Half ester (mass %) | Halogen (mass %) | Catechol family member (mass %) | Degree of coloring (Hazen) (after 30 days) |
|---|---|---|---|---|---|---|---|
| Example 1-1 | 1 | 40 | 93.0 | 0.3 | 0.01 | 0.22 | 30 |
| Example 1-2 | 0.5 | 5 | 92.1 | 1.0 | 0.05 | 0.22 | 35 |
| Example 1-3 | 10 | 5 | 93.3 | 0.001 | 0.05 | 0.22 | 40 |
| Example 1-4 | 1 | 80 | 93.0 | 0.3 | 0.001 | 0.22 | 30 |
| Example 1-5 | 1 | 40 | 93.2 | 0.3 | 0.01 | 0.01 | 35 |
| Example 1-6 | 1 | 40 | 92.1 | 0.3 | 0.01 | 1.0 | 35 |
| Example 1-7 | 1 | 1.5 | 92.9 | 0.3 | 0.7 | 0.22 | 35 |
| Example 1-8 | 1 | 40 | 93.0 | 0.3 | 0.01 | p-methoxyphenol 0.22 | 60 |
| Example 1-9 | 1 | 40 | 93.2 | 0.3 | 0.01 | 0 | 90 |
| Example 1-10 | 1 | 0.5 | 91.0 | 0.3 | 2.2 | 0.22 | 100 |
| Example 1-11 | 1 | 0.5 | 91.2 | 0.3 | 2.2 | 0 | 120 |
| Example 1-12 | 1 | 40 | 93.0 | 0.3 | 0.01 | 0.22 | 30 |
| Comparative Example 1-1 | 0.1 | 0.5 | 88.0 | 2.5 | 2.2 | 0.22 | 200 |
| Comparative Example 1-2 | 0.1 | 1.5 | 90.3 | 2.5 | 0.7 | 0.22 | 150 |

(Notes): In Table 1, as to the mass %, only that of the thiol carboxylate ester is the ratio of it to the composition, and those of the others are the ratios of them to the thiol carboxylate ester. The halogen contents are indicated by conversing the organohalogen compound (chloroform) contents of the Examples and Comparative Example into the halogen atom contents, wherein; those of Examples 1-1 to 1-3, 1-5 to 1-6, 1-8 to 1-9, and 1-12 are rounded up to two decimal places, and that of Example 1-4 is rounded up to three decimal places, and those of Examples 1-7, 1-10 to 1-11 and Comparative Examples 1-1 to 1-2 are rounded up to one decimal place.

COMPARATIVE EXAMPLE 1-3

An amount of 100 parts of the dehalogenated solution (having the bis(2-methacryloylthioethyl) sulfide content of 88.0 mass % and the half ester content of 2.5 mass % relative to this thiol carboxylate ester), as obtained in Comparative Example 1-1, was mixed with 0.5 part of 2,2'-azobis(2,4-dimethylvaleronitrile), and the resultant mixture was cast-polymerized under the same conditions as of Example 1-1, thus obtaining a 3-mm-thick sheet made of the thiol carboxylate ester. This sheet was cut with a diamond cutter to observe whether the cut section was broken, cracked, fused, or not. As a result, in the cut section, there were seen a little breakage and a few cracks, and there also occurred fusion. Therefrom the above-obtained comparative thiol carboxylate ester was found to be bad in polymerizability.

EXAMPLE 2-1

A dehalogenated solution containing the thiol carboxylate ester was obtained in the same way as of Example 1-1 except that the stirring duration, after the completion of the dropwise additions, and the distillation duration of the solvent, were changed and adjusted.

With regard to the resultant dehalogenated solution, the quantitative analysis of its thiol carboxylate ester content, half ester content, and organohalogen compound content and further its heat-resistant discoloring test were carried out in the same way as of Example 1-1. Their results are shown in Table 2.

EXAMPLES 2-2 AND 2-3

Dehalogenated solutions containing the thiol carboxylate ester were obtained in the same way as of Example 2-1 except that the kind of the catechol family member and the amount thereof as added were changed.

With regard to the resultant dehalogenated solutions, the quantitative analyses of their thiol carboxylate ester contents, half ester contents, and organohalogen compound contents and further their heat-resistant discoloring tests were carried out in the same way as of Example 1-1. Their results are shown in Table 2.

TABLE 2

| Kind of catechol family member | Thiol carboxylate ester (mass %) | Half ester (mass %) | Halogen (mass %) | Catechol family member (mass %) | Degree of coloring (Hazen) |
|---|---|---|---|---|---|
| Example 2-1: Methylcatechol | 93.0 | 0.30 | 0.05 | 0.22 | 30 |
| Example 2-2: Di-t-butylcatechol | 93.0 | 0.30 | 0.05 | 0.22 | 35 |
| Example 2-3: Catechol | 93.0 | 0.30 | 0.05 | 1.00 | 35 |

(Notes): In Table 2, as to the mass %, only that of the thiol carboxylate ester is the ratio of it to the composition, and those of the others are the ratios of them to the thiol carboxylate ester. The halogen contents are indicated by converting the organohalogen compound (chloroform) contents into the halogen atom contents and rounding them up to two decimal places.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A thiol carboxylate ester composition, comprising:
   a) a thiol carboxylate ester as shown by general formula (I) below:

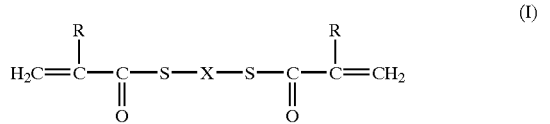

(wherein: R denotes H or —$CH_3$; and X denotes —$CH_2CH_2SCH_2CH_2$—, —$CH_2CH_2OCH_2CH_2$—, or —$CH_2CH_2$—);

b) a half ester as shown by general formula (II) below, of 0.0001 to 2 mass % relative to the thiol carboxylate ester:

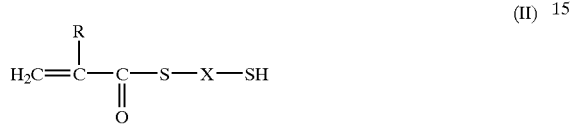

(wherein: R denotes H or —$CH_3$; and X denotes —$CH_2CH_2SCH_2CH_2$—, —$CH_2CH_2OCH_2CH_2$—, or —$CH_2CH_2$—);

c) wherein said composition has a halogen content of not more than 2 mass % relative to the thiol carboxylate ester; and d) wherein said composition includes a polymerization inhibitor, wherein said polymerization inhibitor is a member selected from the group consisting of hydroquinone, phenothiazine, p-methoxyphenol, benzoquinone, hindered amine, and a catechol family member of general formula (4) below:

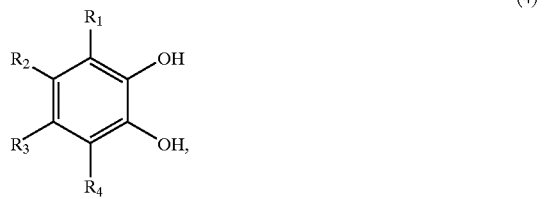

wherein each of $R_1$, $R_2$, $R_3$, and $R_4$ denotes a hydrogen atom, a hydroxyl group, or any alkyl groups having 1 to 4 carbon atoms.

2. A thiol carboxylate ester composition according to claim 1, to which the polymerization inhibitor is added in a ratio of 0.001 to 2 mass % relative to the thiol carboxylate ester.

3. A thiol carboxylate ester composition according to claim 1, which displays a degree of coloring (Hazen) of not more than 120 as a result of storage in an incubator of 40° C. for 30 days.

4. A thiol carboxylate ester composition, comprising:

a) a thiol carboxylate ester as shown by general formula (I) below:

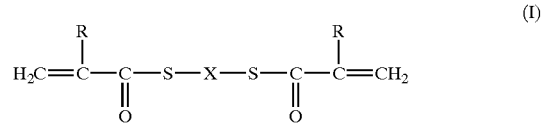

(wherein: R denotes H or —$CH_3$; and X denotes —$CH_2CH_2SCH_2CH_2$—, —$CH_2CH_2OCH_2CH_2$—, or —$CH_2CH_2$—);

b) a half ester as shown by general formula (II) below, of 0.0001 to 2 mass % relative to the thiol carboxylate ester:

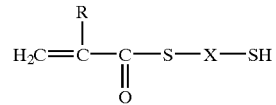

(wherein: R denotes H or —$CH_3$; and X denotes —$CH_2CH_2SCH_2CH_2$—, —$CH_2CH_2OCH_2CH_2$—, or —$CH_2CH_2$—);

c) wherein said composition has a halogen content of 0.0001 to 2 mass % relative to the thiol carboxylate ester; and d) wherein said composition includes a polymerization inhibitor, wherein said polymerization inhibitor is a member selected from the group consisting of hydroquinone, phenothiazine, p-methoxyphenol, benzoquinone, hindered amine, and a catechol family member of general formula (4) below:

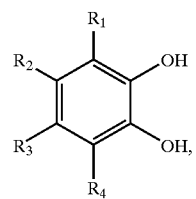

wherein each of $R_1$, $R_2$, $R_3$, and $R_4$ denotes a hydrogen atom, a hydroxyl group, or any alkyl groups having 1 to 4 carbon atoms.

* * * * *